(12) United States Patent
Hyde et al.

(10) Patent No.: US 9,719,906 B2
(45) Date of Patent: Aug. 1, 2017

(54) DETERMINING CONDITIONS IN CENTRIFUGED BLOOD USING MEASURED PRESSURE

(75) Inventors: David D. Hyde, Ontario, NY (US); Michael W. LaCourt, Spencerport, NY (US); Tracy McDonald, Rochester, NY (US); Christopher M. Parobek, Honeoye Falls, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 1242 days.

(21) Appl. No.: 13/366,876

(22) Filed: Feb. 6, 2012

(65) Prior Publication Data

US 2012/0202238 A1    Aug. 9, 2012

Related U.S. Application Data

(60) Provisional application No. 61/439,947, filed on Feb. 7, 2011.

(51) Int. Cl.
| | |
|---|---|
| *G01N 15/00* | (2006.01) |
| *G01N 15/04* | (2006.01) |

(Continued)

(52) U.S. Cl.
CPC ........... *G01N 15/042* (2013.01); *G01N 15/05* (2013.01); *G01N 33/491* (2013.01); *G01N 35/1009* (2013.01); *G01N 2015/055* (2013.01)

(58) Field of Classification Search
CPC ..... G01N 33/491; G01N 15/05; G01N 15/042

(Continued)

(56) References Cited

U.S. PATENT DOCUMENTS

| 4,272,482 A | 6/1981 | Jessop et al. |
|---|---|---|
| 5,111,703 A | 5/1992 | Allen |

(Continued)

FOREIGN PATENT DOCUMENTS

| EP | 0 606 480 A1 | 7/1994 |
|---|---|---|
| EP | 0 981 048 B1 | 11/2003 |

(Continued)

OTHER PUBLICATIONS

Chinese Office Action for CN 201210033058.7; Dated: Sep. 22, 2015; 3 pages.

(Continued)

*Primary Examiner* — Christopher A Hixson
*Assistant Examiner* — Emily Berkeley
(74) *Attorney, Agent, or Firm* — Barclay Damon, LLP

(57) ABSTRACT

A method for determining a condition in a blood sample includes: providing a sample of blood; providing a metering probe having a pump for aspirating and dispensing; inserting the metering probe a selected distance into the blood sample; measuring the pressure between the sample and pump during sample aspiration or sample dispense; comparing the measured pressure with a reference value; and signaling the presence or absence of the condition. A method for confirming or detecting the presence of a selected layer of blood component in a centrifuged blood sample includes: measuring a pressure of a suspected selected layer in a metering probe during aspiration or dispense; comparing the measured pressure with a reference value, wherein if the measured pressure and the reference value are substantially identical then the selected layer of the blood component is confirmed. In a preferred embodiment the reference value is a pre-selected pressure range.

6 Claims, 5 Drawing Sheets

(51) Int. Cl.
*G01N 15/05* (2006.01)
*G01N 33/49* (2006.01)
*G01N 35/10* (2006.01)

(58) Field of Classification Search
USPC .......................................................... 436/148
See application file for complete search history.

(56) References Cited

U.S. PATENT DOCUMENTS

| | | | |
|---|---|---|---|
| 5,133,392 A | | 7/1992 | Hamann |
| 5,143,849 A | | 9/1992 | Barry et al. |
| 5,273,717 A | | 12/1993 | Marvin |
| 5,452,619 A | * | 9/1995 | Kawanabe ............ G01N 33/491 73/863 |
| 5,463,895 A | | 11/1995 | Brentz |
| 5,488,854 A | | 2/1996 | Kawanabe et al. |
| 5,540,081 A | | 7/1996 | Takeda et al. |
| 5,750,881 A | | 5/1998 | Dorenkott et al. |
| 5,814,275 A | | 9/1998 | Lewis et al. |
| 6,060,320 A | | 5/2000 | Dorenkott et al. |
| 6,121,049 A | * | 9/2000 | Dorenkott et al. ............ 436/50 |
| 6,370,942 B1 | * | 4/2002 | Dunfee .............. G01N 35/1016 73/1.74 |
| 6,484,556 B1 | | 11/2002 | Jabobs et al. |
| 6,797,518 B1 | | 9/2004 | Jacobs et al. |
| 7,361,509 B2 | | 4/2008 | Hyde et al. |
| 7,477,997 B2 | * | 1/2009 | Kaplit .................... B01L 3/021 221/10 |
| 2003/0022380 A1 | | 1/2003 | Jakubowicz et al. |
| 2005/0196867 A1 | | 9/2005 | Bower et al. |

FOREIGN PATENT DOCUMENTS

| | | |
|---|---|---|
| EP | 2 006 689 A2 | 12/2008 |
| JP | 2003-533701 | 11/2003 |
| JP | 2010-48594 | 3/2010 |
| WO | WO 01/88549 A1 | 11/2001 |

OTHER PUBLICATIONS

European Search Report for EP 14 195 967.6; Dated: May 13, 2015; 7 pages.

Japanese Office Action for JP 2012-022869; Date: Dec. 15, 2015; 4 pages.

Chinese Office Action for CN 201210033058.7; Dated: May 23, 2016; 6 pages.

* cited by examiner

DETERMINING CONDITIONS IN CENTRIFUGED BLOOD USING MEASURED PRESSURE

CROSS REFERENCE TO RELATED APPLICATION

This patent application is a Non-Provisional of U.S. Provisional Application No. 61/439,947, filed Feb. 7, 2011, the disclosure of which are incorporated by reference in their entirety.

BACKGROUND OF THE INVENTION

The present invention relates to the determination of conditions in centrifuged blood using measured pressure in an aspirate or dispense process. In particular, the present invention relates to detecting or confirming the aspiration of packed red blood cells from centrifuged blood.

Most blood donations are divided (fractionated) into their components: red blood cells, platelets, clotting factors, plasma, antibodies (immunoglobulins), and white blood cells. Depending on the situation, people may receive only the cells from blood, only the clotting factors from blood, or some other blood component. Transfusing only selected blood components allows the treatment to be specific, reduces the risks of side effects, and can efficiently use the different components from a single unit of blood to treat several people.

Packed red blood cells (PRBC), the most commonly transfused blood component, can restore the blood's oxygen-carrying capacity. This component may be given to a person who is bleeding or who has severe anemia. The red blood cells are separated from the fluid component of the blood (plasma) and from the other cellular and cell-like components. This step concentrates the red blood cells so that they occupy less space, thus the term "packed." Red blood cells can be refrigerated for up to 42 days. In special circumstances—for instance, to preserve a rare type of blood—red blood cells can be frozen for up to 10 years. Thus, the ability to separate PRBCs from other components for transfusion is important.

The field of immunohematology is the science of antigens and antibodies as they relate to the management of transfusion by donor and transfusion services. Applications of immunohematology include the definition of blood types, and the identification of unexpected antibodies that may lead to incompatible transfusions and transplants or complications during pregnancy. Both recipient (patient) and donor blood is tested to assure a safe blood transfusion.

Blood typing may be carried out manually or on automated or semi-automated systems such as the ORTHO PROVUE® sold by Ortho-Clinical Diagnostics, Inc.

In immunohematology as well as clinical chemistry, whole blood must sometimes be spun down into layers of its various components by centrifugation before it can be analyzed. The layers are mainly composed of plasma, a buffy coat which contains white blood cells and plasma, and packed red blood cells (PRBC).

Packed red blood cells are important for a variety of reasons in addition to those listed. PRBCs are needed to in order to do some of the types of testing in immunohematology. The PRBCs are used in a diluted form typically in a dilution ratio of 0.8% and 4.0% to the appropriate manufactured saline diluent. To aspirate the PRBCs, the metering probe must go through the plasma layer of the centrifuged blood.

Thus, from both a transfusion and immunohematology perspective, it is important to be able to identify and separate out PRBCs from the other components of blood. Known methods for identifying and separating PRBCs from other components of blood have included operator observations prior to testing (e.g., blood typing) or using an imaging system post testing. Such post testing suffers from lack of accuracy and the need to rerun a test if separation was incomplete or if the wrong layer was aspirated. It is also important from both a transfusion and immunohematology perspective to be able to detect other conditions in centrifuged blood, such as an error condition of incomplete centrifugation, or other error conditions.

There is still a need to be able to distinguish between various layers of blood components, such as a layer of PBRCs from other components of blood after centrifugation and to determine other conditions that may be present in centrifuged blood samples.

SUMMARY OF THE INVENTION

The present invention is directed to a method that addresses the foregoing problems of being able to determine conditions in centrifuged blood, such as identifying a layer of PRBC from other components of centrifuged blood.

One aspect of the invention is directed to a method for determining a condition in a blood sample. The method includes: providing a sample of blood; providing a metering probe having a pump for aspirating and dispensing; inserting the metering probe a selected distance into the blood sample; measuring the pressure between the sample and pump during sample aspiration or sample dispense; comparing the measured pressure with a reference value; and signaling the presence or absence of the condition. In a preferred embodiment, the reference value includes a pressure profile, a pre-selected pressure range, or the slope of a pre-selected portion of a pressure profile.

Another aspect of the invention provides a method for confirming or detecting the presence of a selected layer of blood component in a centrifuged blood sample. The method includes: measuring a pressure of a suspected selected layer in a metering probe during aspiration or dispense; comparing the measured pressure with a reference value, wherein if the measured pressure and the reference value are substantially identical then the selected layer of the blood component is confirmed. In a preferred embodiment the reference value is a pre-selected pressure range.

In another preferred embodiment, the selected layer is packed red blood cells and an additional layer is plasma and the method for confirming or detecting the presence of a selected layer of blood component in a centrifuged blood sample further includes: moving a probe tip of the metering probe and centrifuged blood sample relative to one another to position the metering probe above the centrifuged blood sample; moving the metering probe and sample relative to one another to bring the metering probe towards the surface of the blood sample; detecting the surface of the sample; aspirating plasma from the plasma layer; measuring pressure while aspirating the plasma layer; comparing a reference value and the measured pressure to confirm the layer is plasma; moving the aspirating probe tip into the suspected packed red blood cells layer; aspirating the suspected layer and measuring the pressure; and comparing a reference value and the measured pressure to confirm the aspirated suspected layer is the selected packed red blood cells layer.

Yet another aspect of the invention provides a method for detecting the interface between plasma and packed red blood cells layers in a centrifuged blood sample. The method includes: positioning a metering probe above a centrifuged blood sample; moving the probe and sample relative to one another such that the probe moves towards and enters into the sample; measuring a first pressure at a first depth in the sample; measuring a second pressure at a second depth in the sample; and comparing the first and second pressure to determine if the interface is between the first and second depth.

Further objects, features and advantages of the present invention will be apparent to those skilled in the art from detailed consideration of the preferred embodiments that follow.

DETAILED DESCRIPTION OF PREFERRED EMBODIMENTS

While the various applications for determining a condition in a centrifuged blood sample by measuring pressure, such as confirming or detecting a selected blood component, according to the invention are not limited, a particularly useful application is in the field of immunohematology or blood transfusion. The range of instruments and methodologies that can be used with the present invention is large and is discussed in more detail below.

The present invention uses the difference in viscosity as represented by pressure differences between different conditions in centrifuged blood to determine whether or not a certain condition is present in the sample being tested. For example, in a preferred embodiment, the present invention uses a difference in viscosity between a selected blood component and other components of blood to be able to detect the presence or absence of the selected blood component and to determine that the selected blood component is being aspirated or dispensed during a metering event.

In a preferred embodiment, the present invention uses the difference in viscosity between PRBC (referred to as RBC in the figures) and other components of blood, mainly plasma, to be able to detect the presence of PRBC and to confirm that PRBC are being aspirated or dispensed during a metering event. Much of the remainder of the description herein depicts a blood component as the selected condition, and in particular, plasma or PRBC as the selected blood component. However, the invention is not so limited and any other component of blood may be the selected layer as long as it can be centrifuged into a layer and has a different viscosity than the other layers of blood components. For example, a selected blood component could be the buffy coat layer, which contains white blood cells and platelets. Also, any other condition, which may be determined by a pressure difference between a measured pressure and reference value pressure is also within the scope of the present invention.

The viscosity of PRBC, generally in the range 8-12 centipoises (cps) or higher depending on the concentration of PRBC, is significantly larger than the viscosity of plasma which is generally in the range of less than 2 to 3 cps. The reason that PRBC are believed to have a larger viscosity is due to the higher concentration of solids (i.e., red blood cells) and hence more resistance to flow. Generally, the concentration in a PRBC layer is approximately 80% red blood cells and 20% plasma.

Figure 1:
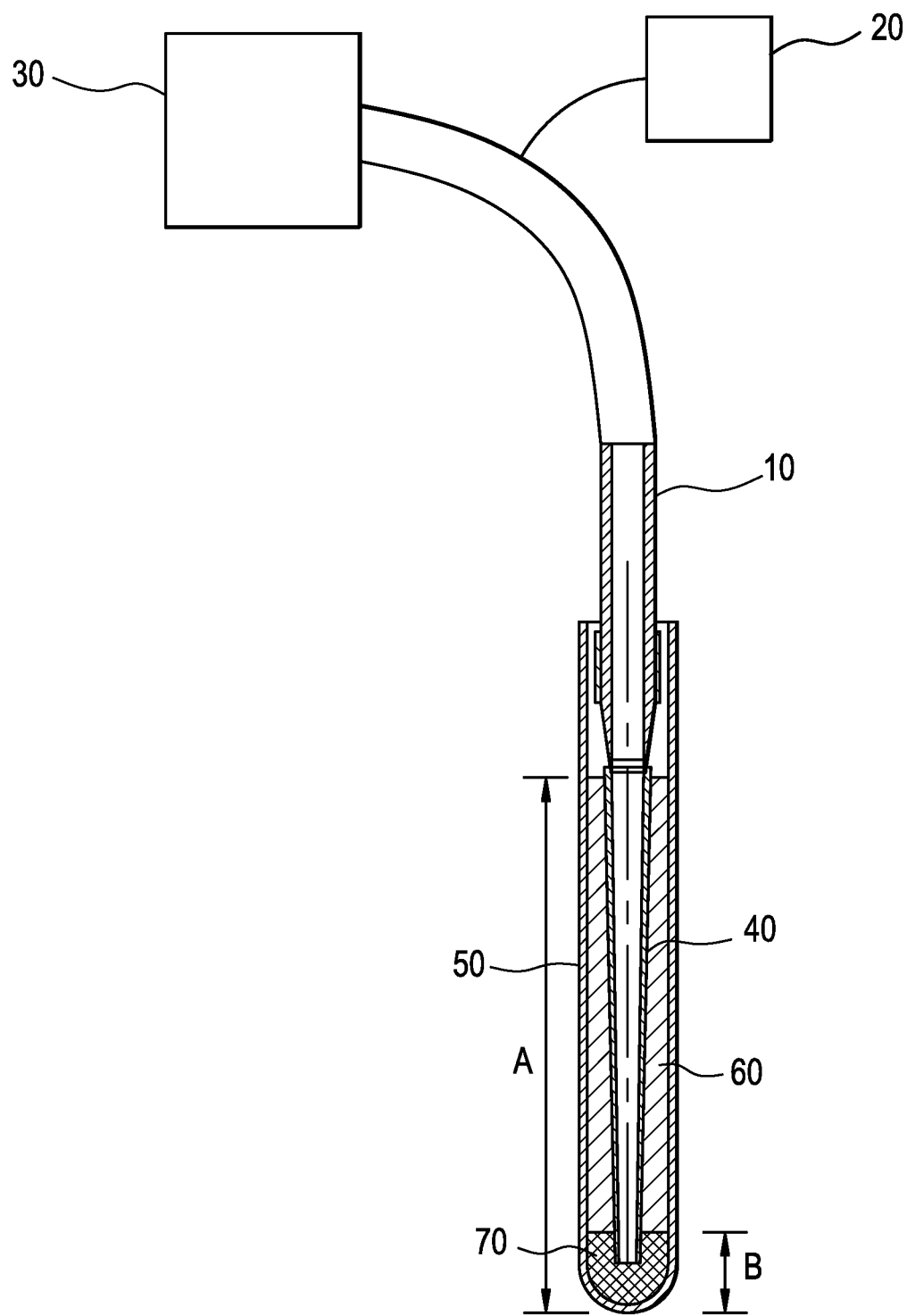
FIG. 1 shows a schematic view of a conventional metering probe and tip in a sample container that can be used according to a preferred embodiment of the invention.
Figure 2:
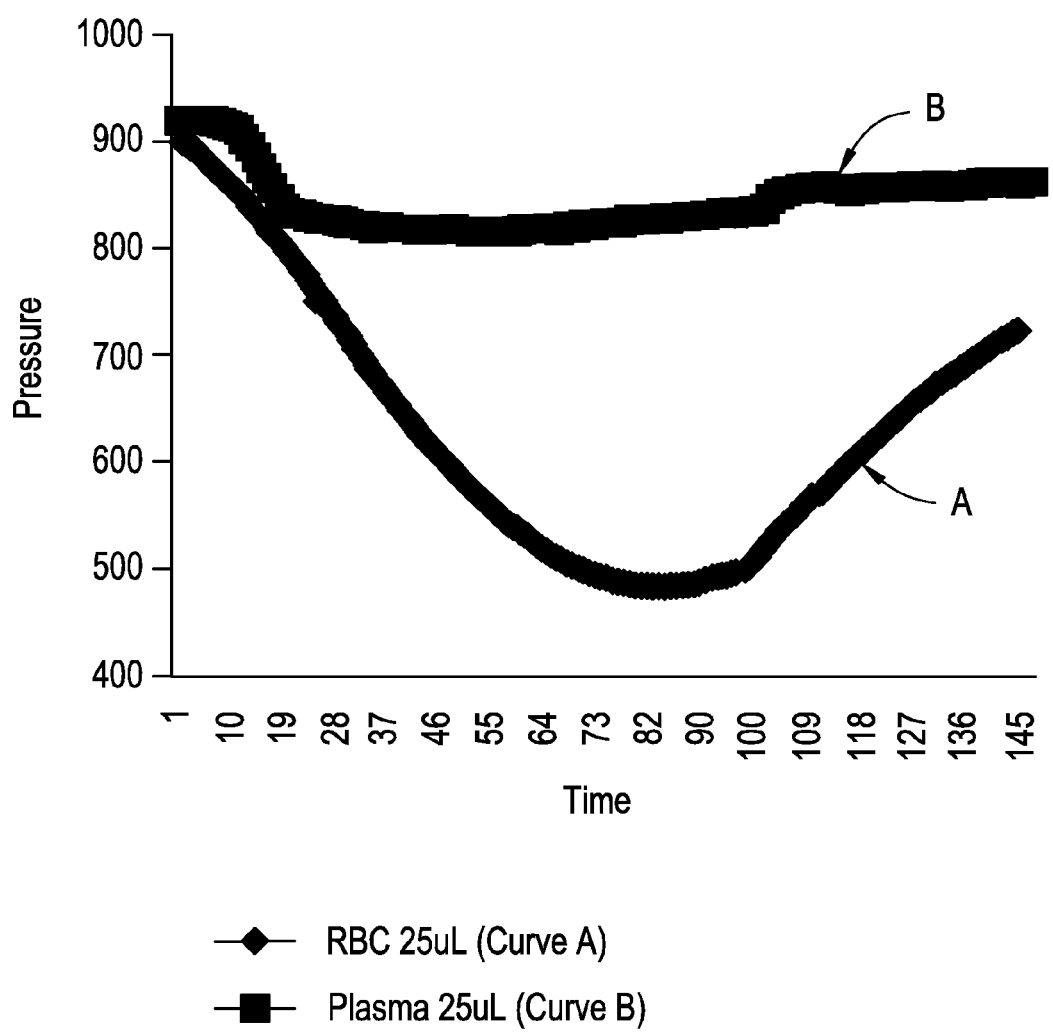
FIG. 2 shows a pressure profile of pressure vs. time for plasma and PRBC for an aspirate process according to a preferred embodiment.

The difference in viscosities between PRBC and plasma will lead to different pressure profiles during a metering event (i.e., aspiration or dispense) due to the greater resistance to flow by the PRBC (assuming other conditions, such as aspirate/dispense rate remain the same). In other words, a greater pressure will have to be applied to PRBC to achieve flow as compared to plasma. FIG. 2 shows the difference in pressure profiles for plasma and PRBC. This pressure can be monitored by a pressure sensor (e.g., a pressure transducer) in a metering system that includes a metering probe that can be used for aspirate and/or dispense. Suitable conventional metering systems that include pressure sensors and metering probes are described for example in U.S. Pat. Nos. 6,484,556; 6,060,320; 5,750,881; 5,540,081 and 7,361,509, all incorporated by reference in their entireties. The only requirement is the ability to measure pressure in the space between the liquid being aspirated or dispensed and the pumping mechanism for the metering equipment. This is generally accomplished using a pressure transducer located between the tip of an aspirating/dispense probe and the pump as shown in FIG. 1. FIG. 1 is a schematic drawing of a combination aspirating/dispense probe that includes proboscis 10, pressure transducer 20 for measuring the pressure between the metering pump 30 and the liquid (in this case a centrifuged blood sample). The probe also includes a disposable metering tip 40 on the end of the proboscis. In this illustration the metering tip is inserted into a test tube 50 in the PRBC near the bottom of the tube. The tube contains centrifuged blood which having a height A and is separated into plasma portion 60 and PRBC portion 70 having a height B.

To carry out the method according the present invention whole blood is obtained and is centrifuged using a centrifuge and techniques well known to those skilled in the art. The whole blood is typically centrifuged in a sample collection container, such as a test tube.

Once the blood has been separated into its constituent layers, the selected layer can be separated out from the rest of the components generally by aspiration. For example, the PRBC layer being the most dense component will be at the bottom of the sample collection container. At this point, depending on the aspect of the method being carried out, the metering probe can be moved to various points in the centrifuged blood.

In one preferred embodiment where the PRBC layer is the selected layer, the metering probe is moved to the vicinity of the bottom of the sample collection container, preferably a few millimeters from the bottom of the container. If the centrifugation has been properly performed, the PRBC will be at the bottom of the container. The pump of the metering probe will activate and begin aspirating the PRBC into the tip. The tip may be disposable or fixed (i.e., permanent). A disposable tip has the advantage of not requiring a complex probe tip wash system and minimizing the chances of carry over between different blood samples.

Typical disposable tips include the MICROTIP™ and VERSATIP™ both sold by Ortho-Clinical Diagnostics, Inc. and are described for example in U.S. Pat. No. 6,797,518 and in U.S. Published Patent Application No. 2003-0022380 A1, both of which are incorporated by reference in their entireties. If the probe tip is fixed, probes and probe washing systems such as those described in U.S. Published Patent Application No. 2005-0196867 A1 can be used.

Upon aspirating the PRBC into the tip a first pressure profile will be generated. The pressure profile is measured by the pressure transducer associated with the metering probe and may be recorded by a computer associated with the metering probe. The entire pressure profile may be used in the comparison described below, or more preferably a portion or select point(s) on the pressure profile can be used. In one preferred embodiment, one or more pressure measurements at known times during a metering event may be recorded. In another embodiment, the slope of a selected portion of the pressure profile may be determined and recorded.

At this point, the first pressure profile (or pressure measurements or slope) generated for the PRBC must be compared with a reference value or pressure. The form of the reference value will depend on what was measured and recorded. For example, if the measured value was the entire pressure profile, then the appropriate comparison would be with a pressure profile and hence the reference value will be a second pressure profile. If the measured value was a selected pressure measurement in the profile, the comparison would be to pressure measurements and hence the reference value could be a single pressure value or a range of pressure that forms an upper and lower pressure limit. Likewise, if the measured value was the slope of a portion of the pressure profile, the comparison would be to a slope of the same portion of the pressure profile. It could also be a combination of two or more of the above.

As noted above, if the measured valued during the metering event was a first pressure profile, it will be compared with a second pressure profile to ensure the PRBC has been aspirated. This second pressure profile can be from multiple sources. The second pressure profile can be a previously measured profile from another blood sample of plasma and/or PRBC that may be stored in a memory device associated with a computer controlling the metering probe. Alternatively, the second pressure profile can be the measured pressure profile of a plasma layer in the same centrifuged blood sample (this will generally be the case since plasma is aspirated first for most test profiles). The computer compares the measured first pressure profile with the second pressure profile. This could also be a combination of several of the above techniques making for a more robust conclusion.

If the second pressure profile is of PRBC and it is substantially identical to the first pressure profile believed to be of PRBC, then this will be an indication or confirmation that PRBC are, in fact, what was aspirated and the aspirated PRBC may then be subsequently used as desired, such as for the uses described above. As used herein, "substantially identical" means that the measured pressure is ≤20%, more preferably ≤10%, and most preferably ≤5% different than the reference value. If the second pressure profile is of plasma and it is significantly different from the first pressure profile believed to be of PRBC, then this will be an indication or confirmation that PRBC are, in fact, what was aspirated and the aspirated PRBC may then be subsequently used as desired, such as for the uses described above. As used herein, "significantly different" means that the measured pressure is ≥25%, more preferably ≥30%, more preferably ≥35% and most preferably ≥40% different than the reference value. Table 1 which shows this concept more graphically is shown below.

TABLE 1

Pressure Profile State Table

|  | Condition 1 | Condition 2 | Condition 3 | Condition 4 |
| --- | --- | --- | --- | --- |
| First Profile | Low Viscosity (Plasma) | High Viscosity (PRBC) | Low Viscosity (Plasma) | High Viscosity (PRBC) |
| Second Profile | Low Viscosity (Plasma) | High Viscosity (PRBC) | High Viscosity (PRBC) | Low Viscosity (Plasma) |
| Outcome (Probe Position) | No Change Plasma Level | No Change PRBC Level | Different PRBC Level | Different Plasma level |

If the pressure profiles do not correspond as described above, then this is an indication that PRBC are not being aspirated and the separation of the blood into its components was not successful or that the probe is at an incorrect metering height or the fluid component levels is not what was anticipated. For example, there may have been an incomplete or no centrifugation that took place. In this instance, the first pressure profile (or other measurement) would be similar to whole blood and such a pressure profile would fall in between that of plasma and PRBC. The metering probe can indicate an error, such as by an alarm or suspending the operation of the metering probe or instrument associated with the metering probe, at which point the operator or instrument can take appropriate action such as conducting a further investigation or starting the process over. Other conditions which may give rise to an error condition are described in more detail below.

While the description above and below involves using a pressure profile as the measured and recorded value, other measurements (e.g., slope, discrete pressure measurements) also noted above can be used. Alternatively, as noted above, as opposed to measuring the entire pressure profile, discrete pressure measurements can be measured at specified time(s) after aspirate or dispense has begun and compared to see if the measured pressure falls within or outside of a predetermined range. The range may be determined by empirical testing.

According to another aspect of the invention both the plasma layer and PRBC layer are aspirated and subsequently used such as for blood typing. In such a case, the detection method can be used to confirm that both layers have been successfully aspirated. As above whole blood samples are centrifuged to separate the red blood cells from the plasma. The samples are presented in the sample collection container for testing/separation possibly with unknown volumes/fluid heights.

A metering probe such as that described above moves horizontally to position itself over the sample and moves down vertically to the surface of the plasma. Although the metering probe is described as moving relative to the sample in this embodiment and other embodiments described herein, it should be understood that the only requirement is for the metering probe and sample to come into contact with one another. This may equally be accomplished by the sample container moving in the direction of a stationary metering probe. In a preferred embodiment, the probe senses the top surface of the plasma. The metering tip can sense the top of the liquid using any number of known techniques such as those described U.S. Pat. Nos. 5,273,717, 5,143,849, 5,133,392, 5,111,703 and 4,272,482.

Once the fluid surface is found, the metering probe will aspirate the desired volume of plasma for subsequent use. During this aspiration step, pressure inside the tip is measured, such as by using a pressure transducer described above and a pressure measurement such as a first pressure profile such as that shown in FIG. 2 is generated. A reference value such as a second pressure profile is generated as described above. The pressure measurement and reference value, such as a first and second pressure profiles, are compared. Depending on whether the second pressure profile is of plasma or PRBC, the pressure profiles will be substantially identical or significantly different. If the comparison between the first and second pressure profiles reveals that plasma has not been aspirated an error signal may be generated as described above. Otherwise, the metering probe then extracts the tip from the fluid and proceeds to dispense the plasma as needed.

After at least some of the plasma layer has been aspirated, the PRBC layer will be aspirated. If it has not already done so, the metering probe disposes of the metering tip used for the plasma aspirate and picks up a new disposable tip. In the case of a non-disposable metering tip, the tip may be washed between the plasma aspirate and the PRBC aspirate. The metering probe moves vertically down into the sample container and through any remaining plasma down to within a few millimeters from the bottom of the sample container described above. The metering probe aspirates the PRBC and measures internal pump/tip pressure to generate a pressure measurement such as a first pressure profile as described above. A reference value such as a second pressure profile is generated as described above. The pressure measurement and reference value, such as the first and second pressure profiles, are compared. Depending on whether the second pressure profile is of plasma or PRBC, the pressure profiles will be substantially identical or significantly different. If the comparison between the first and second pressure profiles reveal that PRBC has not been aspirated an error signal may be generated as described above. Otherwise, the metering probe then extracts the tip from the fluid and proceeds to dispense the PRBC as needed.

While this embodiment has been described with the plasma layer being aspirated first, it is equally feasible to first proceed the PRBC layer, followed by the plasma layer.

According to yet another aspect of the invention, the invention can be used to locate the interface of the plasma/PRBC layers of a centrifuged sample. In practice, a metering probe would be traveling down vertically through the centrifuged sample. During the travel through the sample, sample is aspirated continuously or at preselected points throughout the depth of the sample. The more often the sampling, the more accurate the detection of the interface will be, hence continuous pressure measurement is preferable. When the tip of the metering probe reaches the interface, the pressure measurement will rapidly change, such as by a large change in slope indicating that the interface has been reached.

One useful application of this aspect of the invention is to provide a percent hematocrit value of a patient's sample. The hematocrit (Ht or HCT) or packed cell volume (PCV) or erythrocyte volume fraction (EVF) is the proportion of blood volume that is occupied by red blood cells. It is normally about 48% for men and 38% for women. It is considered an integral part of a person's complete blood count results, along with hemoglobin concentration, white blood cell count, and platelet count. The volume of packed red blood cells divided by the total volume of the blood sample gives the PCV. Because a tube is used, this can be calculated by measuring the lengths of the layers. Using FIG. 1 as an example, the HCT or PCV value can be determined by dividing the PRBC layer B by the total volume of blood sample A.

Now reference will be made to the non-limiting embodiments shown in the figures. FIG. 2 shows a pressure profile of pressure as represented by voltage vs. time (msec) for plasma and PRBC for an aspirate process. The pressure profile for plasma is shown in squares (■) and labeled as curve B, and the pressure profile for PRBC is shown in diamonds (♦) and labeled as curve A. In this example, 25 µL of plasma and 25 µL of PRBC were aspirated from a centrifuged blood sample. The PRBC having a higher viscosity will have the greater change in pressure as FIG. 2 clearly shows.

Figure 3:
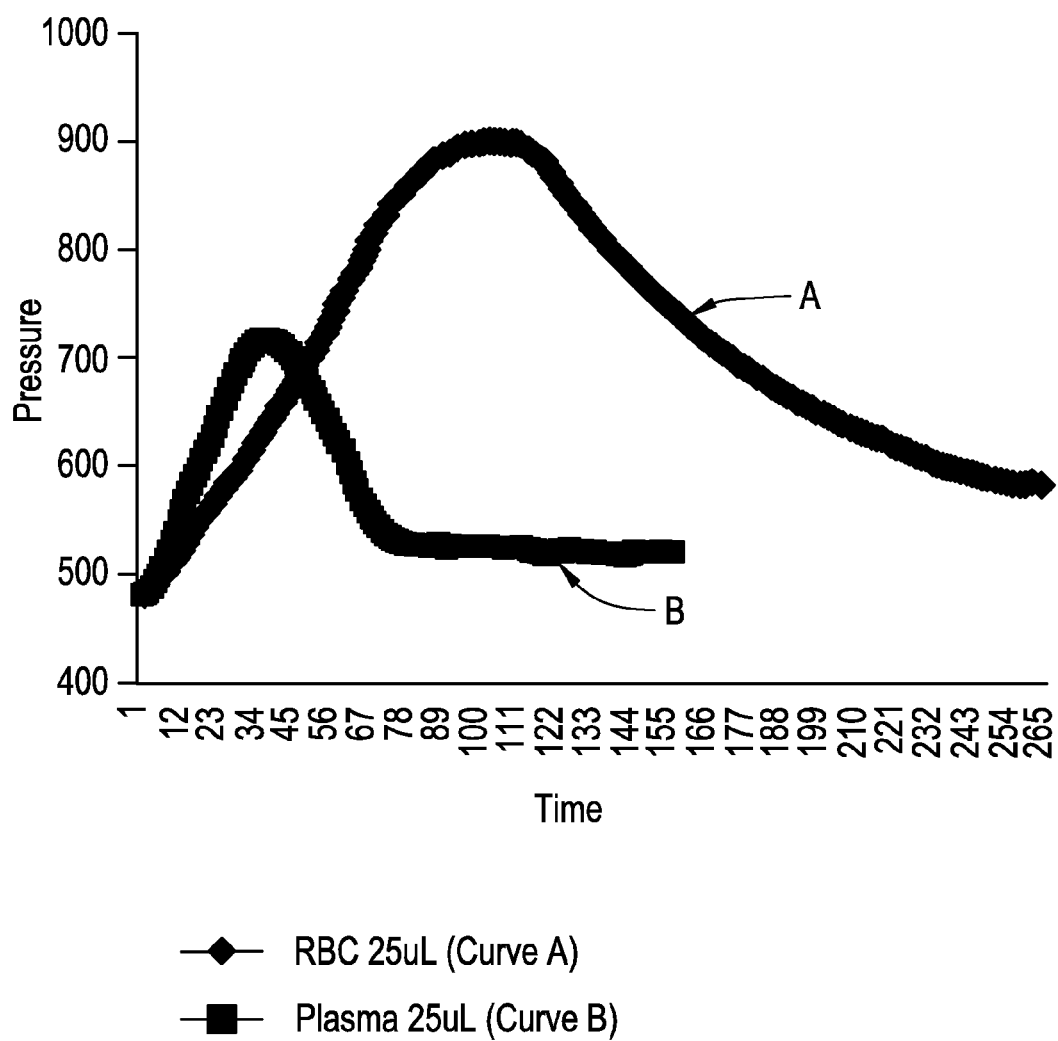
FIG. 3 shows a pressure profile of pressure vs. time for plasma and PRBC for a dispense process according to a preferred embodiment.

FIG. 3 shows a pressure profile of pressure (voltage) vs. time (msec) for plasma and PRBC for a dispense process. The pressure profile for plasma is shown in squares (■) and labeled as curve B, and the pressure profile for PRBC is shown in diamonds (♦) and labeled as curve A. In this example, 25 µL of plasma and 25 µL of PRBC were dispensed from a centrifuged blood sample. The PRBC being more viscous will have the greater change in pressure as FIG. 3 clearly shows.

Figure 4:
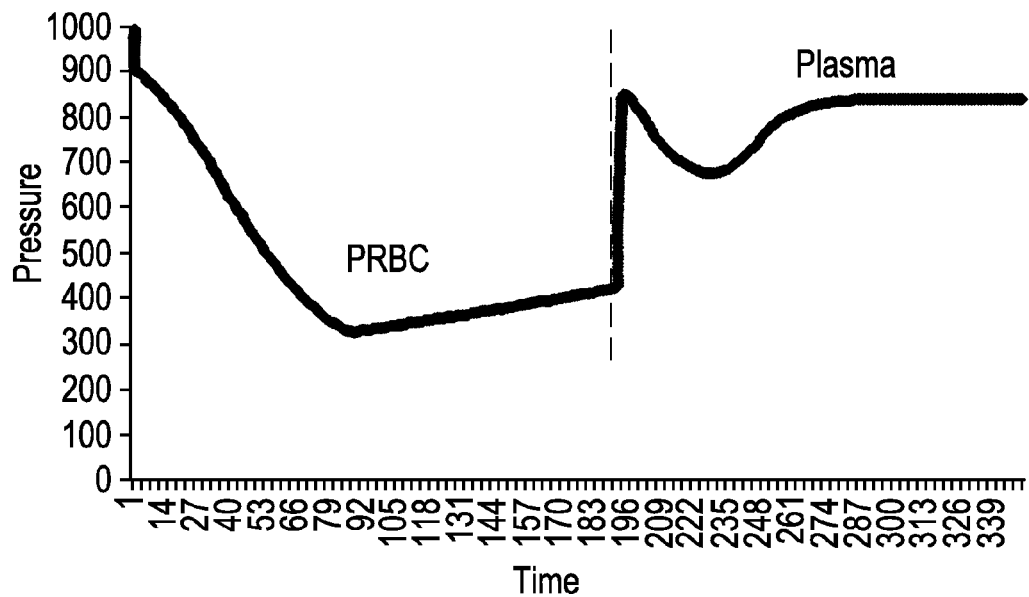
FIG. 4 shows a pressure profile of pressure vs. time for plasma and PRBC for a sequential aspiration of PRBC and plasma in the same tip according to a preferred embodiment.

FIG. 4 shows an example where both plasma and PRBC are aspirated sequentially during the same aspirate process using the same disposable tip The beginning of the aspiration as shown on the left hand side of the graph is PRBC, while the second part of the aspiration as shown in the right hand side of the graph is plasma. The Y-axis indicates the relative pressure difference between the two different fluid types in a normal sample that has been centrifuged so that all the red blood cells are at the bottom of the sample container. The X-axis is time (msec). As FIG. 4 shows, there is a sharp discontinuity in pressure when the interface is reached. This sequential aspiration of PRBC and plasma is particularly useful for locating the interface between the plasma and PRBC layers.

Figure 5:
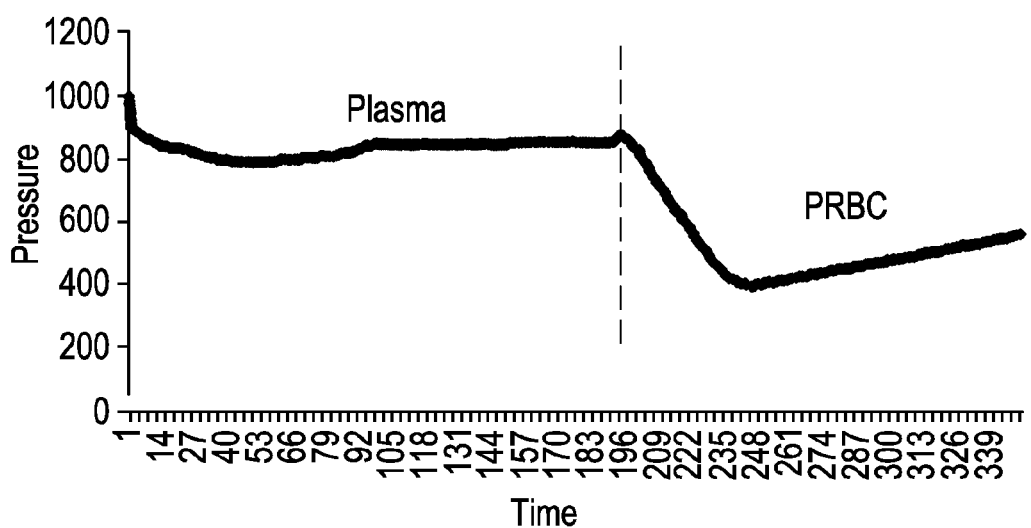
FIG. 5 shows a pressure profile of pressure vs. time for plasma and PRBC for a sequential aspiration of plasma and PRBC in the same tip according to a preferred embodiment.

FIG. 5 is much the same as FIG. 4 except the aspiration order is reversed. This indicates that independent of the fluid type aspiration order, the pressure differential can be used to identify what fluid type is where. In fact, this method can be used to search for the plasma to PRBC interface which, among other things, can be used to determine hemocrit values for a particular patient.

Figure 6:
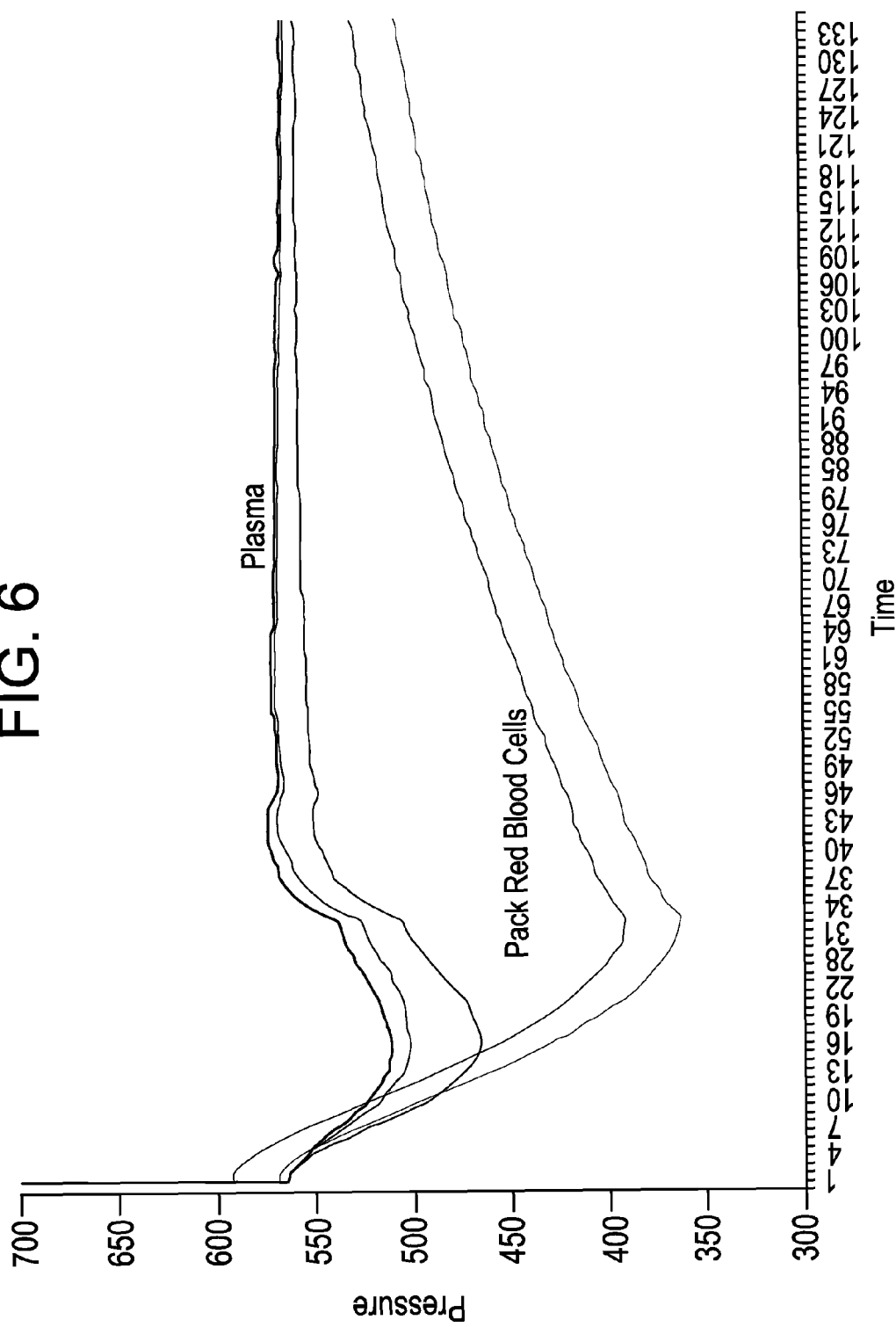
FIG. 6 shows various pressure profiles of pressure vs. time for plasma and PRBC for an aspirate process according to a preferred embodiment.

FIG. 6 shows various pressure profiles of pressure vs. time for plasma and PRBC for a aspirate process in which 200 µL of a diluent fluid is already in the tip before aspirating 10 µL of plasma or PRBC. The first three profiles from the top are for plasma and the lower two profiles are for PRBC. As the graphs show, the difference between the pressure profiles of plasma vs. PRBC is very evident, even with the diluent already in the tip. This is a particularly useful find because PRBCs are typically diluted before adding them to the test elements. Based on the finding above, one aspect of the invention provides a streamlined approach for combining PRBCs with diluents. More specifically, according to a preferred embodiment, a tip is inserted onto a probe and moved to a source of diluent. A selected amount of diluent is aspirated into the tip. After the diluent is aspirated into the tip, the tip is moved to a centrifuged blood sample. The probe is moved to the bottom of the centrifuged blood where the PRBC layer is expected. Using the present invention, the metering system confirms that the layer being aspirated is, in fact, PRBC. After aspiration of the PRBC into the tip that includes the diluents, the diluent and PRBC are dispensed into a well and mixed. The same tip will then dispense the diluted PRBCs into the test elements.

According to yet another aspect of the invention, the present invention can be used to determine other conditions that may be present in a centrifuged blood sample. For example, measuring a pressure difference, or lack thereof, can be used to determine if a sample was properly centrifuged. If there was no or improper centrifugation the pressure measurement would be the same or similar for a whole blood sample and there would be little or no difference between the pressure measurement from the top of the sample to the bottom of the sample. Alternatively, the pressure measurement can be compared to a reference value such as a pre-selected pressure range. If the pre-selected pressure range is for PRBC or platelets and the pressure measurement is outside of the pre-selected range, then this is an indication of improper centrifugation. Alternatively, if the pre-selected range is the pressure that would be for an incomplete centrifugation (e.g., pressure range for whole blood) then the pressure measurement would be within the pre-selected range.

Other conditions that can be determined by measuring pressure and comparing with a reference value such as another pressure profile or pre-selected pressure range can include determining whether or not there has already been a previous separation of blood components. For example, if the plasma layer has already been separated from the PRBC layer and removed from the sample container, then pressure measurements will correspond to those expected for a PRBC layer regardless of the probe position in the sample. If the plasma layer was being sought, then the lack of a pressure measurement corresponding to such would trigger an error condition. The same of course would hold true for only a plasma layer being present and the PRBC layer being sought.

Still another condition that could be determined by measuring pressure is whether fibrinogen is being picked up by the tip of the metering probe. When fibrinogen is aspirated into the probe along with the fluid, the fibrinogen will create a resistance to flow (i.e., tend to make the fluid act more viscous) that will require a greater pressure by the metering pump to aspirate the fluid. It is this greater resistance to flow and the ability to measure the resulting pressure that allows fibrinogen (or any other particulate) to be detected in the fluid layer being aspirated. To accomplish such detection, a metering probe is directed into a layer of a centrifuged blood sample. Upon aspirating the plasma layer the measured pressure or profile is compared to a reference value of the fluid without fibrinogen. If the measured pressure indicates a higher viscosity, then it is likely that fibrinogen or other particulate has been aspirated into the metering probe along with the plasma. In such as case, an error condition can be indicated.

If an error condition is indicated, then as described above, the metering probe can indicate an error, such as by an alarm or suspending the operation of the metering probe or instrument associated with the metering probe, at which point the operator or instrument can take appropriate action such as conducting a further investigation or starting the process over.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. A method of determining a condition in a centrifuged blood sample, comprising:
   providing a sample of centrifuged blood separated into a plasma portion at the top of the centrifuged sample and a packed red blood cells portion at the bottom of the centrifuged sample;
   providing a metering probe having a pump for aspirating and dispensing;
   inserting the metering probe a selected distance into the blood sample to the bottom of the centrifuged sample until the metering probe contacts the packed red blood cells portion;
   measuring the pressure between the sample and pump during sample aspiration or sample dispense and generating a first pressure profile;
   comparing at least a portion of the first pressure profile with a reference value relating to a second pressure profile; and
   signaling the presence or absence of the condition, wherein the condition is an error condition caused by an incomplete centrifugation when the measured pressure is outside of the reference value.

2. A method as claimed in claim 1, wherein the reference value is selected from the group consisting of the entire second pressure profile, a pre-selected portion of the second pressure profile, or the slope of a pre-selected portion of the second pressure profile.

3. The method as claimed in claim 2, in which the second pressure profile is that taken of a previously measured pressure profile taken of another centrifuged sample.

4. The method as claimed in claim 3, in which the second pressure profile is taken in the plasma portion of the another centrifuged sample.

5. The method as claimed in claim 3, in which the second pressure profile is taken in the packed red blood cells portion of the another centrifuged sample.

6. A method of determining a condition in a centrifuged blood sample, comprising:
   providing a sample of centrifuged blood separated into a plasma portion at the top of the centrifuged sample and a packed red blood cells portion at the bottom of the centrifuged sample;
   providing a metering probe having a pump for aspirating and dispensing;
   inserting the metering probe a selected distance into the blood sample to the bottom of the centrifuged sample until the metering probe contacts the packed red blood cells portion;
   measuring the pressure between the sample and pump during sample dispense and generating a first pressure profile;
   comparing at least a portion of the first pressure profile with a reference value relating to a second pressure profile; and
   signaling the presence or absence of the condition, wherein the condition is an error condition caused by an incomplete centrifugation, and if the measured pressure is outside of the reference value, then the error condition is signaled.

* * * * *